(12) United States Patent
Choi et al.

(10) Patent No.: US 10,793,516 B2
(45) Date of Patent: Oct. 6, 2020

(54) METHOD FOR SELECTIVELY SYNTHESIZING CATIONIC LIPIDS

(71) Applicant: Samyang Biopharmaceuticals Corporation, Seoul (KR)

(72) Inventors: Sungwon Choi, Daejeon (KR); Hye Yeong Nam, Seongnam-si (KR); Min-Hyo Seo, Yongin-si (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 15/781,493

(22) PCT Filed: Dec. 29, 2016

(86) PCT No.: PCT/KR2016/015525
§ 371 (c)(1),
(2) Date: Jun. 5, 2018

(87) PCT Pub. No.: WO2017/116188
PCT Pub. Date: Jul. 6, 2017

(65) Prior Publication Data
US 2018/0346410 A1    Dec. 6, 2018

(30) Foreign Application Priority Data
Dec. 30, 2015 (KR) .......... 10-2015-0189843

(51) Int. Cl.
*C07C 237/10* (2006.01)
*C07C 231/02* (2006.01)
(Continued)

(52) U.S. Cl.
CPC .......... *C07C 237/10* (2013.01); *C07C 231/02* (2013.01); *C07C 231/12* (2013.01); *C07C 237/06* (2013.01)

(58) Field of Classification Search
CPC .... C07C 237/10; C07C 231/02; C07C 231/12
(Continued)

(56) References Cited

U.S. PATENT DOCUMENTS

| 5,744,355 A | 4/1998 | Weinshilboum et al. |
| 6,133,199 A | 10/2000 | Soula et al. |

(Continued)

FOREIGN PATENT DOCUMENTS

| CN | 104826543 | | 8/2015 |
| CN | 104826543 A | * | 8/2015 |

(Continued)

OTHER PUBLICATIONS

Whitehead, K. A. et al, "Synergistic Silencing: Combinations of Lipid-like Materials for Efficacious siRNA Delivery", Molecular Therapy, 2011 [Electronic publishing: Jul. 12, 2011], vol. 19, No. 9, pp. 1688-1694.

(Continued)

*Primary Examiner* — Deborah D Carr
(74) *Attorney, Agent, or Firm* — Lex IP Meister, PLLC

(57) ABSTRACT

Disclosed is a method capable of selectively synthesizing cationic lipids by controlling the introduction rate of a fatty acid group with respect to an oligoalkyleneamine by the change of reaction conditions.

20 Claims, 3 Drawing Sheets

(51) Int. Cl.
    *C07C 237/06*   (2006.01)
    *C07C 231/12*   (2006.01)
(58) Field of Classification Search
    USPC .......................................................... 554/69
    See application file for complete search history.

(56) References Cited

U.S. PATENT DOCUMENTS

2004/0188047 A1   9/2004   Nakamura et al.
2015/0328152 A1   11/2015  La et al.

FOREIGN PATENT DOCUMENTS

| JP | 04-235148 | | 8/1992 |
|---|---|---|---|
| JP | H04235148 A | * | 8/1992 |
| KR | 10-2009-0088362 | | 8/2009 |
| KR | 10-1308591 | | 9/2013 |
| WO | 1999-005914 | | 2/1999 |
| WO | 2002-081410 | | 10/2002 |
| WO | 2008-042973 | | 4/2008 |
| WO | 2012-091523 | | 7/2012 |

OTHER PUBLICATIONS

Akinc, A. et al., "A Combinatorial Library of Lipid-Like Materials for Delivery of RNAi Therapeutics", Nature Biotechnology, 2008 [Electronic publishing: Apr. 27, 2008], vol. 26, No. 5, pp. 561-569.
Ming Zhou et al., "Synthesis of Bis[N,N'-(alkylamideethyl)ethyl] Triethylenediamine Bromide Surfactants and Their Oilfield Application Investigation", Journal of Surfactants and Detergents, 2012, vol. 15, No. 3, pp. 309-315.
Y. Y. Jiang et al., "Inhibition of Iron Corrosion in HCl Solutions by N-[2-[(2-Aminoethyl) Amino] Ethyl]-9-Octadecenamide", Corrosion, 2013, vol. 69, No. 7, pp. 672-680.
W.I.A. El-Dougdoug, "Synthesis and surface active properties of cationic surface active agents from rice bran oil", Grasas Y Aceites, Jan. 1, 1999, vol. 50, No. 5, pp. 385-391, XP055596267.
Duan, Ming et al., "Synthesis of a Cationic Gemini Surfactant with Amide Group", Chinese Journal of Applied Chemistry, May 2004, vol. 21, No. 5, pp. 538-540.
EPO, Communication of EP 16882140.3 dated May 20, 2020.
Daqiang Xu et al., "An expeditious synthesis of a biscyclam with an aromatic linker", Tetrahedron Letters, vol. 37, No. 30, pp. 5301-5304, May 4, 1996.

* cited by examiner

[Fig. 1]
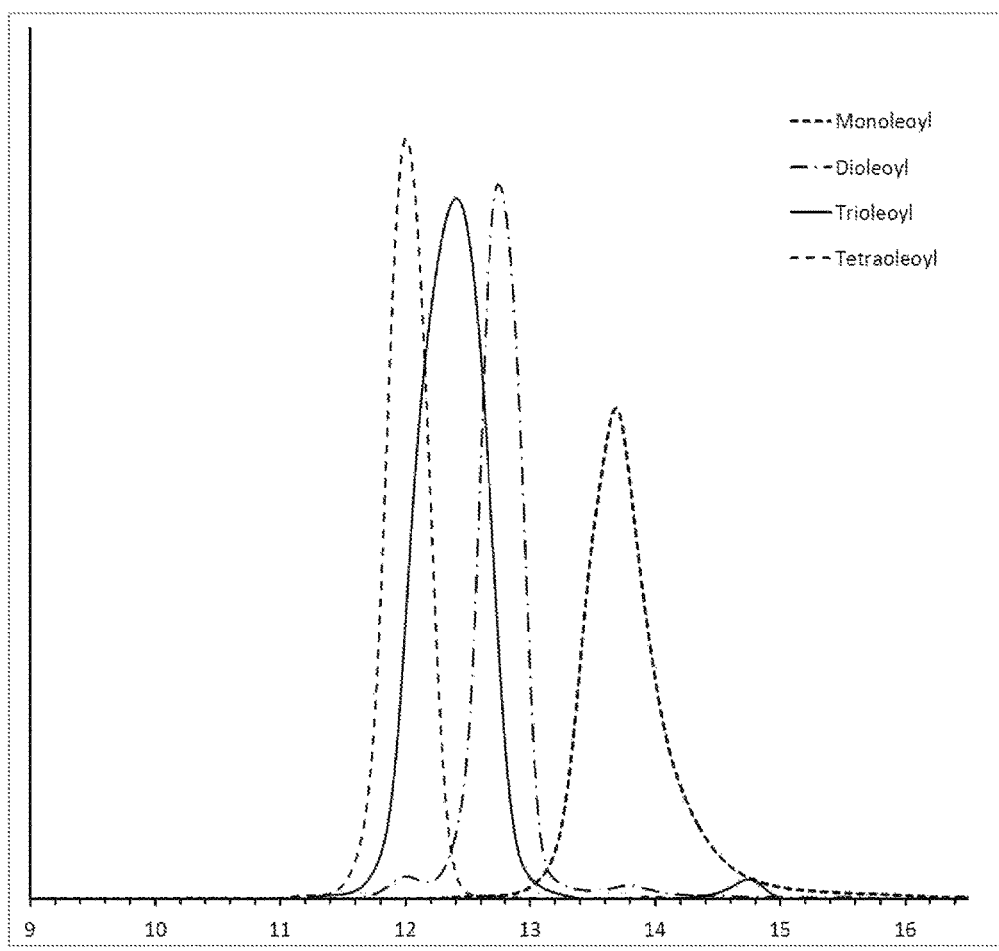

[Fig. 2]
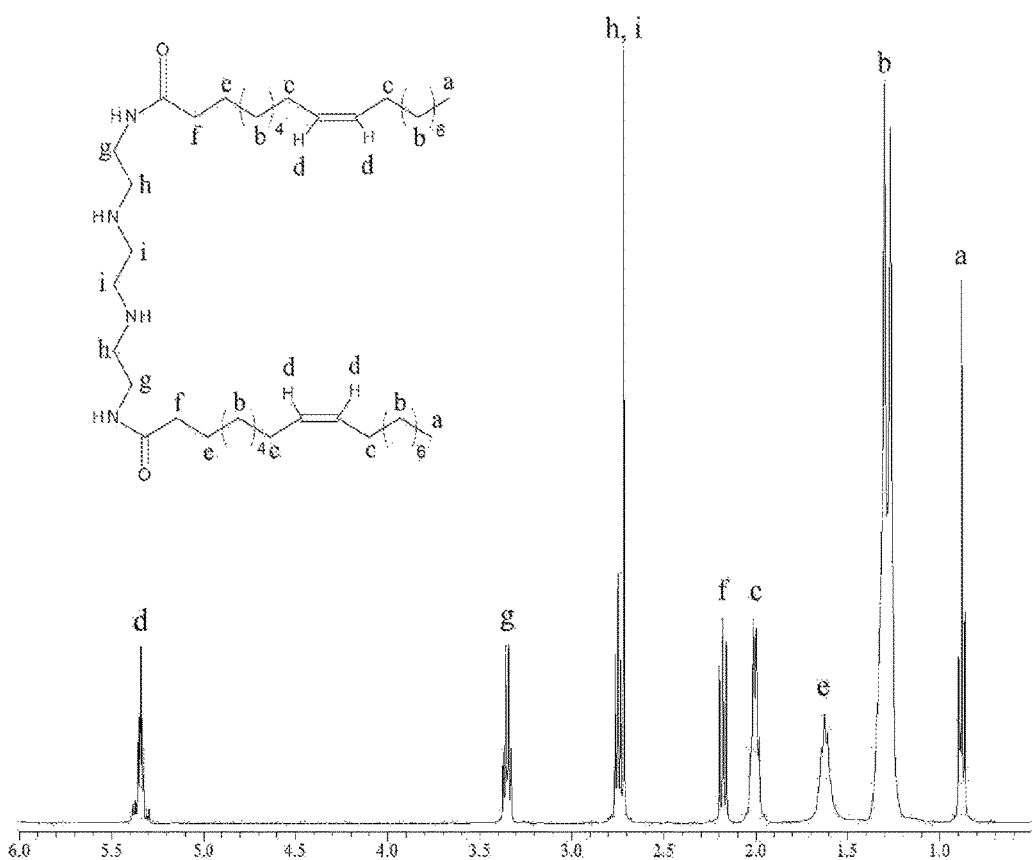

[Fig. 3]
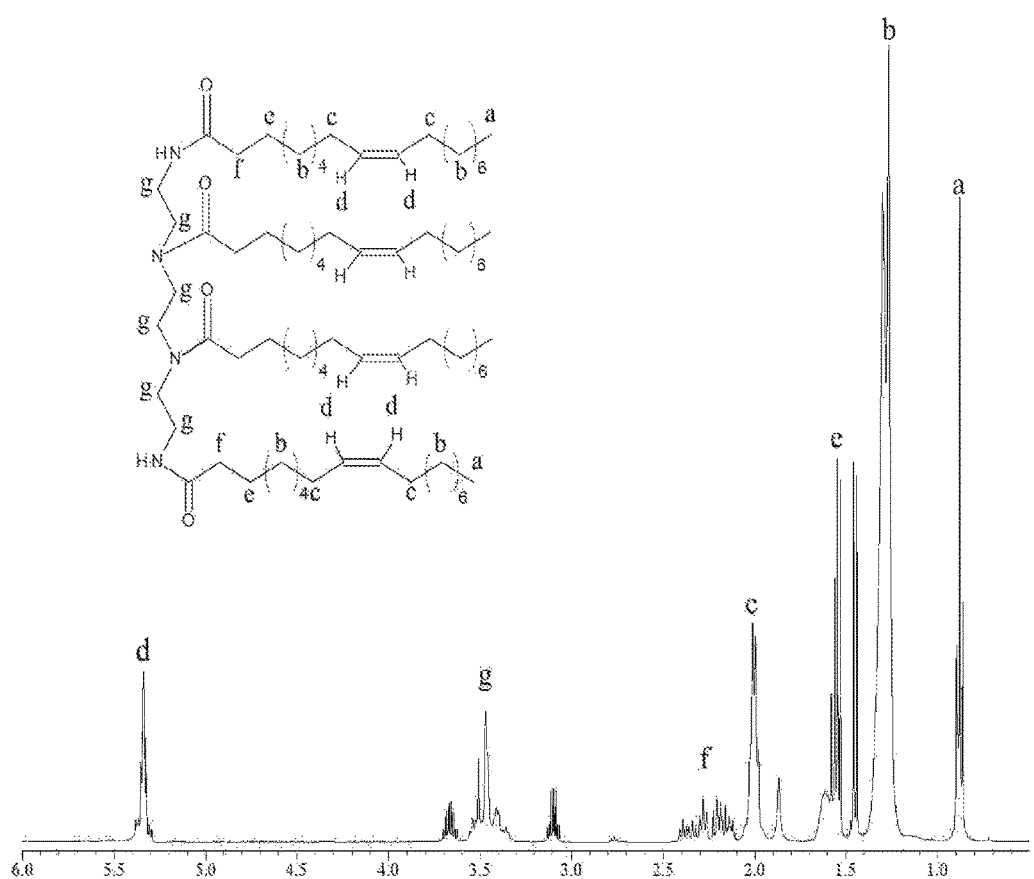

METHOD FOR SELECTIVELY SYNTHESIZING CATIONIC LIPIDS

TECHNICAL FIELD

The present disclosure relates to a synthesis method that allows control of the introduction rate and introduction position of a fatty acid group which is introduced into an oligoalkyleneamine during synthesis of cationic lipids.

BACKGROUND ART

Until now, the synthesis of cationic lipids in which saturated or unsaturated fatty acid groups are introduced into an amine group of the oligoalkyleneamine has been reported to introduce lipids into primary amines at both ends of the oligoalkyleneamine (see U.S. Pat. Nos. 9,220,779, 5,744,355, etc.). However, under the synthesis conditions of the prior art, since the fatty acid groups react nonspecifically with primary and secondary amine groups of the oligoalkyleneamine, it is impossible to react lipids selectively with only amine groups at one or both ends of the oligoalkyleneamine by such conventional synthesis methods. Therefore, a mixture having different lipid introduction rates is synthesized, and a mixture having different cationic lipid compositions can be synthesized for each reaction. It is very difficult to separate and purify the thus synthesized mixture of cationic lipids into lipids having the same introduction rates, respectively, and there is a problem that many processes are required. Therefore, there is a need for a method that can produce an oligoalkyleneamine-based cationic lipid in an environmentally-friendly and economical manner, and can selectively introduce lipids into an amine group.

DETAILED DESCRIPTION OF THE INVENTION

Technical Problem

Under these circumstances, the present inventors have conducted intensive studies on selective synthesis methods capable of introducing fatty acid groups into oligoalkyleneamines at desired positions and introduction rates during the synthesis of cationic lipids as described above. As a result, the inventors have unexpectedly found that, when changing conditions of oligoalkyleneamine and fatty acid derivative to be reacted, it is possible to obtain a cationic lipid having the desired introduction rate and position of fatty acid groups in a simple, economical and environmentally friendly manner, thereby completing the present invention.

In view of the above, one object of the present invention is to provide a synthesis method of a cationic lipid represented by Formula 1 that can selectively introduce a fatty acid group into a primary or secondary amine group of oligoalkylene amine and can control the introduction rate of the fatty acid to be introduced.

Another object of the present invention is to provide a method capable of efficiently purifying cationic lipids.

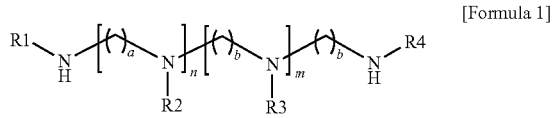

[Formula 1]

in the above formula, the definition of the substituents is as defined below.

Advantageous Effects

The method for synthesizing a cationic lipid according to the present invention can control the introduction rate of the fatty acid group to the oligoalkyleneamine by merely adjusting the synthesis conditions unlike a conventional method. Therefore, unlike the conventional method in which a mixture of cationic lipids having different lipid introduction rates are synthesized at the time of synthesis, since it is possible to synthesize a cationic lipid, which consistently has high purity and uniform introduction rate, purification process with high difficulty is unnecessary. In addition, the synthesis and purification steps are simple, and economical efficiency in mass production is high. Thus, it is very useful for forming an intracellular delivery complex capable of enhancing stability in body fluids together with anionic drugs such as nucleic acid or anionic active ingredients, or for preparing cationic lipids capable of forming liposomes, micelles, emulsions, and nanoparticle drug delivery system.

BRIEF DESCRIPTION OF DRAWINGS

FIG. 1 shows the results of measurement (GPC) of the change in the molecular weight according to the change in the number of fatty acid groups.

FIG. 2 shows the results of proton nuclear magnetic resonance spectroscopy ($^1$H NMR) analysis of 1,6-dioleoyl triethylenetetramide.

FIG. 3 shows the results of proton nuclear magnetic resonance spectroscopy ($^1$H NMR) analysis of tetraoleoyl triethylenetetramide.

DETAILED DESCRIPTION OF THE EMBODIMENTS

In one aspect for achieving the above object, the present invention relates to a method capable of synthesizing a cationic lipid represented by Formula 1 with high purity by controlling the introduction rate of a fatty acid group.

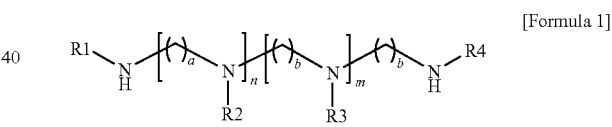

[Formula 1]

Specifically, the present invention is characterized by reacting an oligoalkyleneamine represented by Formula 2 with a fatty acid alkyl ester represented by Formula 3.

[Formula 2]

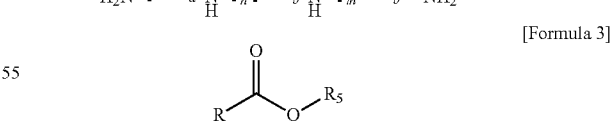

[Formula 3]

in the above formulae 1 to 3, n and m are independently 0 to 12, with the proviso that $1 \leq n+m \leq 12$, a and b are independently 1 to 6, R1, R2, R3 and R4 are independently hydrogen or saturated or unsaturated fatty acid group having 12 to 26 carbon atoms, with the proviso that at least one of R1 and R4 is saturated or unsaturated fatty acid group having 12 to 26 carbon atoms, R is saturated or unsaturated hydrocarbon having 11 to 25 carbon atoms, and R5 is an alkyl group having from 1 to 14 carbon atoms.

In order to keep the density of the fatty acid group high and to minimize the cytotoxicity induced by cations, it is preferable that n and m have the numerical value and range as described above.

In addition, with respect to the R and R1 to R4, if the number of carbon atones in the saturated or unsaturated hydrocarbon is less than 11, the hydrophobic interaction between the hydrocarbon chains can decrease, and thus a formulation stable with the anionic drug cannot be formed. On the other hand, if the number of carbon atoms is larger than 25, the hydrophobic interaction between the hydrocarbons will increase, and thus a formulation excessively stable with the anionic drug will form, whereby the in vivo dissociation of the drug will decrease, leading to a decrease in the efficacy of the drug. In addition, the curvature of the hydrocarbon chains will increase due to an increase in cis double bonds, and thus the resulting formulation will have low density and thus low stability.

In a preferred embodiment, in the selective synthesis method according to the present invention, a cationic lipid of Formula 1 wherein one of R1 and R4 is hydrogen and R2 and R3 are each hydrogen can be prepared by adjusting the molar ratio (oligoalkyleneamine/fatty acid alkyl ester) of the oligoalkyleneamine of Formula 2 to fatty acid alkyl ester of Formula 3 to more than 1 to 20 or less, preferably 3 or more to 8 or less.

In another preferred embodiment, in the selective synthesis method according to the present invention, a cationic lipid of Formula 1 wherein R1 and R4 are fatty acid groups having 12 to 26 carbon atoms and R2 and R3 are hydrogen can be prepared by adjusting the molar ratio of the fatty acid alkyl ester of Formula 3 to the oligoalkyleneamine of Formula 2 to 1 or more to 5 or less, preferably 1.5 or more to 4 or less.

In another preferred embodiment, in the selective synthesis method according to the present invention, a cationic lipid of Formula 1 wherein R1, R2, R3 and R4 are a fatty acid group having 12 to 26 carbon atoms can be prepared by adjusting the molar ratio of the fatty acid alkyl ester of Formula 3 to the oligoalkyleneamine of Formula 2 to more than 5 to 20 or less, preferably 6 or more to 10 or less.

In the above-described synthesis method according to the present invention, the reaction is carried out without using an organic solvent during the reaction of the oligoalkyleneamine with the fatty acid alkyl ester.

In yet another aspect, the present invention provides a method for preparing a cationic lipid of Formula 1 wherein R1 and R4 are a fatty acid group having 12 to 26 carbon atoms and one of R2 and R3 is hydrogen, the method comprising a step of reacting the cationic lipid. of Formula 1 wherein R1 and R4 are a fatty acid group having 12 to 26 carbon atoms and R2 and R3 are hydrogen with a fatty acid alkyl of Formula 3 to prepare a cationic lipid of Formula 1 wherein R1 and R4 are a fatty acid group having 12 to 26 carbon atoms and one of R2 and R3 is hydrogen.

Preferably, n and m are independently 0 to 9, with the proviso that $1 \leq n+m \leq 10$.

Preferably, a and b may be 2 to 4.

Preferably, R1, R2, R3, and R4 may be independently satura fatty acid group having 14 to 22 carbon atoms.

Preferably, one or more of R1, R2, R3 and R4 may be selected from the group consisting of lauroyl, myristoyl, palmitoyl, stearoyl, arachidoyl, behenoyl, lignoceroyl, cerotoyl, myristoleoyl, palmitoleoyl, sapienoyl, oleoyl, linoleoyl, arachidonoyl, eicosapentaenoyl, erucoyl, docosahexaenoyl, and cerotoyl.

In the process for preparing a cationic lipid of Formula 1 wherein R1 and R4 are fatty acid groups having 12 to 26 carbon atoms and one of R2 or R3 is hydrogen, it is desirable that the molar ratio of the fatty acid alkyl ester to the cationic lipid of Formula 1 wherein R1 and R4 are fatty acids having 12 to 26 carbon atoms and R2 and R3 are hydrogen is 0.5 or more to 20 or less, preferably 0.7 or more to 10 or less, more preferably 1 or more to 5 or less.

In the present invention, the oligoalkyleneamine of Formula 2 is specifically oligoethyleneamine. More specifically, it may be at least one selected from the group consisting of diethylenetriamine, triethylenetetramine, tetraethylenepentamine, pentaethylenehexamine, hexaethyleneheptamine, heptaethyleneoctamine, octaethylenenonamine, nonaethylenedecamine, decaethyleneundecamine, undecaethylenedodecamine, dodecaethylenetridecamine and tridecaethylenetetradecamine, but is not limited thereto. Preferably, it is at least one selected from the group consisting of triethylenetetramine, tetraethylenepentamine, pentaethylenehexamine and hexaethyleneheptamine As described above, when the oligoalkyleneamine of Formula 2 and the fatty acid alkyl ester of Formula 3 are reacted at the above equivalent ratio, a high-purity cationic lipid can be synthesized by adjusting the hydrocarbon introduction rate in the produced cationic lipid.

According to the method of the present invention, the cationic lipid can be easily synthesized at a high yield by using a fatty acid derivative such as inexpensive oligoalkyleneamine and fatty acid alkyl ester, which is environmentally friendly and economical. In addition, it is advantageous in that the lipid synthesized through the above reaction has a low solubility in a nonpolar organic solvent and thus is easily precipitated, so that the purification process of the synthesized product is very simple.

Therefore, in another preferred embodiment, the present invention may further include a step of adding a nonpolar organic solvent to the cationic lipid of Formula 1 produced by the above synthesis method, precipitating and separating unreacted materials to purify the cationic lipid. Preferably, the nonpolar organic solvent may be an alkane or ether having 4 to 12 carbon atoms, more preferably hexane, heptane or diethyl ether, but is not limited thereto.

In another preferred embodiment, the present invention may further include a step of dissolving the cationic lipid of Formula 1 produced by the above synthesis method by adding a nonpolar organic solvent, adding an acid thereto to separate the cationic lipid as an acid addition salt into the aqueous layer from the organic solvent, neutralizing the separated lipid, and extracting it with a nonpolar organic solvent, followed by separation and purification. Further, the preferred nonpolar organic solvent may be chloroform or dichloromethane, but is not limited thereto.

As described above, since the cationic lipid of Formula 1 produced by the synthesis method according to the present invention itself exhibits low solubility, easily precipitates and exhibits a uniform introduction rate, the purification method of the present invention using this point has the advantage in that it is economical, environmentally friendly and simple as compared with the conventional purification method of cationic lipids.

Since the cationic lipid synthesized and/or purified according to the present invention retains a positively charged state in cells because the amine group of the oligoalkyleneamine exists in a positively charged form at a hydrogen ion concentration (pH) of a neutral region which is a normal in vivo environment. Therefore, the cationic lipid not only makes it possible to form a complex with an anionic drug containing a negatively charged nucleic acid at neutral pH, such as in vivo, and to increase contact with negatively charged target cell membranes. Thus, the cationic lipids of the present invention can be used to produce various forms of anionic drug delivery formulations, such as liposomes, micelles, emulsions, and nanoparticles for nucleic acid delivery applications.

Hereinafter, the present invention will be described in more detail with reference to the following examples. However, these examples are provided herein for illustrative purposes only and should not be used to limit the scope of the present invention in any manner.

EXAMPLE 1

Synthesis of 1-monoleoyl triethylenetetramide 5.00 g (33.34 mmol) of triethylenetetramine and 2.00 g (6.69 mmol) of methyl oleate were placed in a round bottom flask and then allowed to react with stirring with a magnetic bar at 65° C. under nitrogen for 5 days.

After completion of the reaction, the reaction product was dissolved in 150 mL of diethyl ether, and then sodium chloride (NaCl) was added to 30 mL of 1 M sodium hydroxide (NaOH) solution in a separating funnel, and the reaction mixture was washed three times to remove unreacted triethylenetetramine. The upper organic solvent layer in the separating funnel was heated and distilled under reduced pressure with a distillation condenser.

The finally obtained product was analyzed by HP1100 series gel chromatography using Shodex KF-801 and KF-802 columns in 0.5% v/v trimethylamine-tetrahydrofuran mobile phase at a flow rate of 1 mllmin. The results of the analysis are shown in FIG. 1. In addition, the degree of introduction of an oleoyl group in deuterated chloroform was analyzed with a Bruker AVANCE DPX 400 $^1$H nuclear magnetic resonance spectrometer. The molecular weight of the cationic lipid synthesized under the conditions of MeOH: 5 mM ammonium formate-0/25% formic acid (70:30) was analyzed using Agilent Technologies 646 Triple quad mass spectrometer. Through the above analysis, it was confirmed that the oleoyl group was introduced to one end of the triethylenetetramine. The yield was 73.8%, and 1.1 equivalents of oleoyl groups were introduced into triethylenetetramine. Based on GPC, the purity was confirmed to be 96.7%.

EXAMPLE 2

Synthesis of 1,6-dioleoyl triethylenetetramide 0.50 g (3.34 mmol) of triethylenetetramine and 2.00 g (6.69 mmol) of methyl oleate were placed in a round bottom flask and then allowed to react with stirring with a magnetic bar at 65° C. under nitrogen for 5 days.

After completion of the reaction, the process of adding 15 mL of hexane to the reaction product to precipitate 1,6-dioleoyltriethylenetetramide and extracting unreacted methyl oleate was repeated three times. The precipitated lipid was precipitated and separated from hexane by centrifugation, recovered and vacuum dried.

The molecular weight of the purified cationic lipid and the degree of introduction of oleoyl groups were confirmed by gel chromatography, proton nuclear magnetic resonance spectroscopy and mass spectrometry in the same manner as in Example 1. The results of the gel chromatography and proton nuclear magnetic resonance spectroscopy are shown in FIGS. 1 and 2, respectively. The yield was 79.9%, and 2.06 equivalents of oleoyl groups were introduced into the triethylenetetramine. Based on GPC, the purity was confirmed to be 95.7%.

EXAMPLE 3

Synthesis of 1,3,6-Trioleoyl triethylenetetramide 1,3,6-trioleoyl triethylenetetramide was synthesized by further reacting 1,6-dioleoyl triethylenetetramide synthesized in Example 2 with methyl oleate. Specifically, 400 mg (578.3 μmol) of 1,6-dioleoyl triethylenetetramide and 173.2 mg (578.3 μmol) of methyl oleate were dissolved in 100 mL of dimethylformamide and then allowed to react with refluxing and stirring at 90° C. under nitrogen for 5 days.

After completion of the reaction, the reaction product was vacuum dried to remove dimethylformamide, and then 50 mL of hexane was added to precipitate unreacted 1,6-dioleoyl triethylenetetramide and then centrifuged. Subsequently, the separated supernatant was vacuum dried, to which 10 mL of 1M hydrogen chloride (HCl) was added, and the synthesized 1,3,6-trioleoyl triethylenetetraamide was converted in the form of a mono-HCl salt (1,3,6-trioleoyl triethylenetetramide.1HCl). After that, 50 mL of chloroform was added thereto and unreacted methyl oleoyl was extracted and removed in a separating funnel. The acidic aqueous solution in which the cationic lipid was dissolved was neutralized with sodium hydroxide, and the lipid was extracted with chloroform and vacuum dried.

The molecular weight of the purified and finally obtained product and the degree of introduction of oleoyl groups were confirmed by using gel chromatography, proton nuclear magnetic resonance spectroscopy and mass spectrometry in the same manner as in Example 1. The results of the gel chromatography are shown in FIG. 1. It was confirmed that the yield was 47.5% and 2.94 equivalents of oleoyl groups were bonded to the triethylenetetramine. Based on GPC, the purity was confirmed to be 94.3%.

EXAMPLE 4

Synthesis of Tetraoleoyl triethylenetetramide 0.50 g (3.34 mmol) of triethylenetetramine and 8.00 g (26.76 mmol) of methyloleate were placed in a round bottom flask and then allowed to react with stirring with a magnetic bar at 65° C. under nitrogen for 5 days.

After completion of the reaction, the process of adding 15 mL of hexane to the reaction product to precipitate tetraoleoyl triethylenetetramide and extracting unreacted methyloleate was repeated three times. The precipitated tetraoleoyl triethylenetetramide lipid was precipitated and separated from hexane by centrifugation, recovered and vacuum dried.

The molecular weight of the purified cationic lipid and the degree of introduction of oleoyl groups were confirmed by gel chromatography, proton nuclear magnetic resonance spectroscopy and mass spectrometry in the same manner as in Example 1. The results of the gel chromatography and proton nuclear magnetic resonance spectroscopy are shown in FIGS. 1 and 3, respectively. The yield was 89.1% and 4.05 equivalents of oleoyl groups were introduced into the triethylenetetramine. Based on GPC, the purity was confirmed to be 99.4%.

The invention claimed is:

1. A method for preparing a cationic lipid represented by Formula 1, comprising reacting an oligoalkyleneamine represented by Formula 2, with a fatty acid alkyl ester represented by Formula 3 to prepare the cationic lipid of Formula 1:

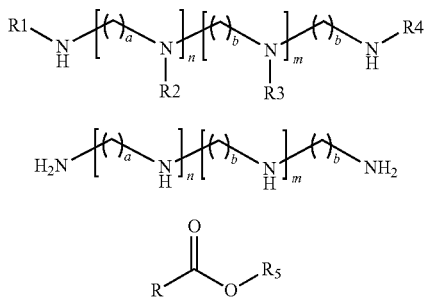

in the formulae 1 to 3,
n and m are independently 0 to 12, with the proviso that 1≤n+m≤12,
a and b are independently 1 to 6,
one of R1 and R4 is saturated or unsaturated fatty acid group having 12 to 26 carbon atoms, and the other of R1 and R4 is hydrogen,
R2 and R3 are each independently hydrogen,
R is saturated or unsaturated hydrocarbon having 11 to 25 carbon atoms, and R5 is an alkyl group having from 1 to 14 carbon atoms,
wherein the molar ratio of the oligoalkyleneamine to the fatty acid alkyl ester is adjusted to 3 or more to 8 or less to obtain the cationic lipid of Formula 1, and wherein the oligoalkyleneamine of Formula 2 and the fatty acid alkyl ester of Formula 3 are reacted in the absence of an organic solvent.

2. A method for preparing a cationic lipid represented by Formula 1, comprising reacting an oligoalkyleneamine represented by Formula 2, with a fatty acid alkyl ester represented by Formula 3 to prepare the cationic lipid of Formula 1, and adding a nonpolar organic solvent after the reaction to purify the cationic lipid, wherein the nonpolar organic solvent is an alkane or ether having 4 to 12 carbon atoms:

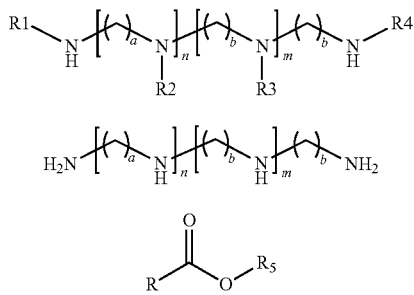

in the Formulae 1 to 3,
n and m are independently 0 to 12, with the proviso that 1≤n+m≤12,
a and b are independently 1 to 6,
R1 and R4 are each independently saturated or unsaturated fatty acid group having 12 to 26 carbon atoms,
R2 and R3 are each independently hydrogen,
R is saturated or unsaturated hydrocarbon having 11 to 25 carbon atoms, and
R5 is an alkyl group having from 1 to 14 carbon atoms,
wherein the molar ratio of the fatty acid alkyl ester to the oligoalkyleneamine is adjusted to 1 or more to 5 or less to obtain the cationic lipid of Formula 1, wherein the oligoalkyleneamine of Formula 2 and the fatty acid alkyl ester of Formula 3 are reacted in the absence of an organic solvent.

3. A method for preparing a cationic lipid represented by Formula 1, comprising reacting an oligoalkyleneamine represented by Formula 2, with a fatty acid alkyl ester represented by Formula 3 to prepare the cationic lipid of Formula 1:

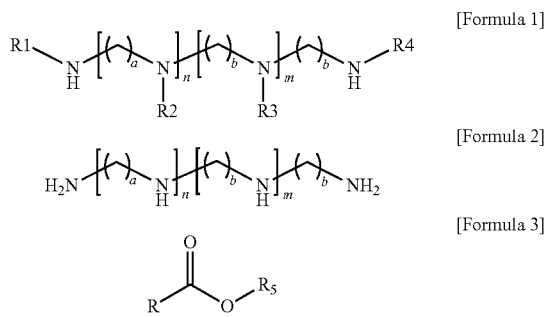

in the Formulae 1 to 3,
n and m are independently 0 to 12, with the proviso that 1≤n+m≤12,
a and b are independently 1 to 6,
R1, R2, R3 and R4 are each independently saturated or unsaturated fatty acid group having 12 to 26 carbon atoms,
R is saturated or unsaturated hydrocarbon having 11 to 25 carbon atoms, and
R5 is an alkyl group having from 1 to 14 carbon atoms,
wherein the molar ratio of the fatty acid alkyl ester to the oligoalkyleneamine is adjusted to more than 5 to 20 or less to obtain the cationic lipid of Formula 1, wherein the oligoalkyleneamine of Formula 2 and the fatty acid alkyl ester of Formula 3 are reacted in the absence of an organic solvent.

4. A method for preparing a cationic lipid of Formula 1 of claim 1 where R1 and R4 are saturated or unsaturated fatty acid group having 12 to 26 carbon atoms, and one of R2 and R3 is hydrogen, wherein the method comprises
reacting the cationic lipid of Formula 1 defined in claim 3 where R1 and R4 are saturated or unsaturated fatty acid group having 12 to 26 carbon atoms and R2 and R3 are hydrogen, with a fatty acid alkyl ester of Formula 3 defined in claim 3 to prepare the cationic lipid of Formula 1 where R1 and R4 are saturated or unsaturated fatty acid group having 12 to 26 carbon atoms and one of R2 and R3 is hydrogen, wherein the molar ratio of the fatty acid alkyl ester to the cationic lipid of Formula 1 is 0.5 or more to 20 or less.

5. The method for preparing a cationic lipid according to claim 1, wherein n and m are independently 0 to 9, with the proviso that 1≤n+m≤10.

6. The method for preparing a cationic lipid according to claim 1, wherein n and m are independently 2 to 4.

7. The method for preparing a cationic lipid according to claim 1, wherein the oligoalkyleneamine of Formula 2 is oligoethyleneamine.

8. The method for preparing a cationic lipid according to claim 1, further comprising adding a nonpolar organic solvent after the reaction, precipitating and separating the cationic lipid from the unreacted materials to purify the cationic lipid.

9. The method for preparing a cationic lipid according to claim 8, wherein the nonpolar organic solvent is an alkane or ether having 4 to 12 carbon atoms.

10. The method for preparing a cationic lipid according to claim 4, further comprising dissolving the cationic lipid in a nonpolar organic solvent, adding an acid to separate the cationic lipid as an acid addition salt in the aqueous layer from the organic solvent, neutralizing the separated cationic lipid, and extracting and purifying the neutralized cationic lipid with a nonpolar organic solvent.

11. The method for preparing a cationic lipid according to claim 2, wherein n and m are independently 0 to 9, with the proviso that $1 \leq n+m \leq 10$.

12. The method for preparing a cationic lipid according to claim 2, wherein n and m are independently 2 to 4.

13. The method for preparing a cationic lipid according to claim 2, wherein the oligoalkyleneamine of Formula 2 is oligoethyleneamine.

14. The method for preparing a cationic lipid according to claim 2, further comprising adding a nonpolar organic solvent after the reaction, precipitating and separating the cationic lipid from the unreacted materials to purify the cationic lipid.

15. The method for preparing a cationic lipid according to claim 14, wherein the nonpolar organic solvent is an alkane or ether having 4 to 12 carbon atoms.

16. The method for preparing a cationic lipid according to claim 3, wherein n and m are independently 0 to 9, with the proviso that $1 \leq n+m \leq 10$.

17. The method for preparing a cationic lipid according to claim 3, wherein n and m are independently 2 to 4.

18. The method for preparing a cationic lipid according to claim 3, wherein the oligoalkyleneamine of Formula 2 is oligoethyleneamine.

19. The method for preparing a cationic lipid according to claim 3, further comprising adding a nonpolar organic solvent after the reaction, precipitating and separating the cationic lipid from the unreacted materials to purify the cationic lipid.

20. The method for preparing a cationic lipid according to claim 19, wherein the nonpolar organic solvent is an alkane or ether having 4 to 12 carbon atoms.

\* \* \* \* \*